United States Patent [19]

Taylor et al.

[11] 4,401,125
[45] Aug. 30, 1983

[54] STETHOSCOPE SECURING PAD

[75] Inventors: Rebecca S. Taylor, Mundelein; John A. Pavlo, Hanover Park, both of Ill.

[73] Assignee: The Kendall Company, Boston, Mass.

[21] Appl. No.: 304,395

[22] Filed: Sep. 21, 1981

[51] Int. Cl.³ .............................................. A61B 7/02
[52] U.S. Cl. ..................................... 128/715; 128/773; 128/798; 128/639; 181/131
[58] Field of Search ........ 128/715, 701, 635, 639–641, 128/644, 773, 798, 802–803; 181/131, 137, DIG. 1

[56] References Cited

U.S. PATENT DOCUMENTS

| | | | |
|---|---|---|---|
| 2,685,881 | 8/1954 | Kelly | 128/644 |
| 3,170,459 | 2/1965 | Phipps et al. | 128/640 |
| 3,498,291 | 3/1970 | Bunn | 128/644 |
| 3,566,860 | 3/1971 | Moe, Jr. | 128/641 |
| 3,867,925 | 2/1975 | Ersek | 181/131 X |
| 3,976,848 | 8/1976 | Estes | 181/DIG. 1 |
| 4,166,465 | 9/1979 | Esty et al. | 128/303.13 |
| 4,270,544 | 6/1981 | Gilden et al. | 128/640 |
| 4,308,870 | 1/1982 | Arkans | 128/715 X |

Primary Examiner—Kyle L. Howell
Assistant Examiner—Angela D. Sykes
Attorney, Agent, or Firm—Powell L. Sprunger

[57] ABSTRACT

A pad for securing the head of a stethoscope to a patient's skin comprising, a generally annular sheet of flexible material larger than the head and having an outer edge, an inner edge defining an opening smaller than the head of the stethoscope, a slot extending from the outer edge to the inner edge, a back surface, a front surface, and adhesive on the front surface of the sheet.

7 Claims, 6 Drawing Figures

STETHOSCOPE SECURING PAD

BACKGROUND OF THE INVENTION

The present invention relates to pads for securing a stethoscope to the skin of a patient.

The use of stethoscopes is well known in the medical field. During use, the head of the stethoscope is placed against the patient's body, and the sounds arising within the patient's body are transmitted through a tube of the stethoscope to the physician's ears. Thus, the stethoscopes are utilized to detect and study the sounds in the patient's body. During certain medical procedures, the stethoscope is maintained against the patient's body for extended periods of time, and it is desirable to secure the stethoscope against the body.

SUMMARY OF THE INVENTION

A principal feature of the present invention is the provision of a pad for securing a stethoscope to a patient's skin.

In one form, the pad of the present invention comprises, a generally annular sheet of flexible material larger than a head of the stethoscope and having an outer edge, an inner edge defining an opening smaller than the head of the stethoscope, a slot extending from the outer edge to the inner edge, a back surface, a front surface, and adhesive on the front surface of the sheet. The first embodiment of the pad is utilized for a stethoscope having a head, a stem connected to the head, and a tube connected to the stem and spaced from the head. Another form of the pad comprises, a generally rectangular sheet of flexible material having a pair of side edges, a pair of end edges connecting the side edges, a cut-out in one of the end edges intermediate the side edges and defining a pair of flaps intermediate the cut-out and side edges, a back surface, a front surface, and adhesive on the front surface of the sheet. The second form of the pad is utilized for a stethoscope having a head, a stem connected to the head, and a tube adjacent the head connected to the stem.

A feature of the present invention is that in the first form of the pad the stem of the stethoscope may be passed through the slot of the central opening to position the stethoscope in the pad.

Another feature of the invention is that the adhesive of the pad may be secured to the head and to the skin surrounding the head in order to maintain the stethoscope in place.

Yet another feature of the invention is that the second form of the pad may be positioned over the tube of the stethoscope, with the stethoscope stem received in the cut-out.

Still another feature of the invention is that the adhesive of the pad may be secured to the tube and head of the stethoscope, and may be secured to the skin surrounding the tube and head in order to maintain the stethoscope in place.

Further features will become more fully apparent in the following description of the embodiments of this invention and from the appended claims.

DESCRIPTION OF THE PREFERRED EMBODIMENTS

Figure 1:
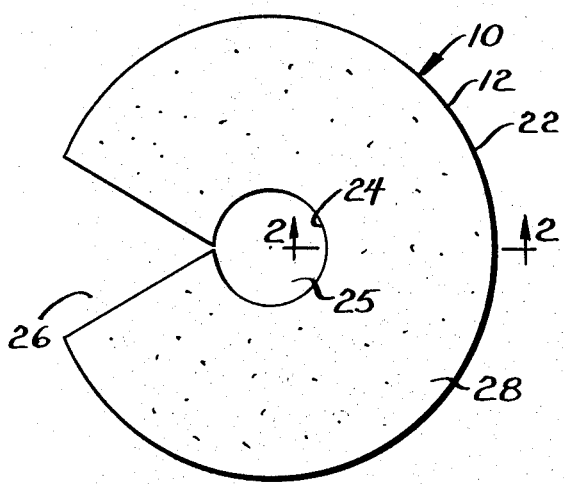
FIG. 1 is a plan view of a securing pad of the present invention.
Figure 2:
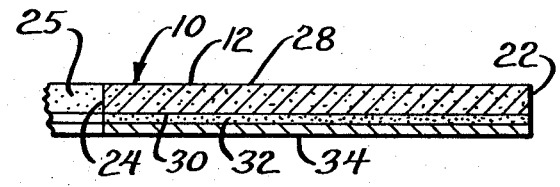
FIG. 2 is a fragmentary sectional view taken substantially as indicated along the line 2—2 of FIG. 1.
Figure 3:
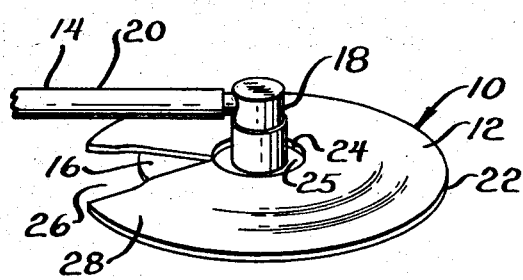
FIG. 3 is a fragmentary perspective view showing the pad as utilized to secure the head of a stethoscope to a patient's skin.

Referring now to FIGS. 1-3, there is shown a securing pad generally designated 10 comprising a generally annular sheet 12 of flexible material, such as closed cell polyethylene foam. The pad 10 is utilized with a stethoscope 14 of the type having a head 16, a stem 18 connected to the head 16, and a tube 20 connected to the stem 18 and spaced from the head 16.

The sheet 12 has a generally circular outer edge 22 defining dimensions of the sheet 12 larger than the head 16 of the stethoscope 14. The sheet 12 also has a generally circular inner edge 24 defining a central opening 25 having dimensions larger than the stem 18 but smaller than the head 16 of the stethoscope 14. The sheet 12 has a generally V-shaped slot 26 extending between the outer edge 22 and the inner edge 24, with the slot 26 being tapered from the outer edge 22 toward the inner edge 24. The sheet 12 has a back surface 28, an opposed front surface 30, and a pressure-sensitive adhesive 32 on the front surface 30 of the sheet 12. The pad 10 also has a release sheet 34 of suitable material covering the adhesive 32 on the sheet 12.

In use, the release sheet 34 is peeled from the adhesive 32 in order to expose the adhesive 32. Next, the stem 18 of the stethoscope 14 is inserted through the slot 26 into the opening 25 to position the head 16 of the stethoscope 14 beneath the sheet 12, after which the adhesive 32 surrounding the opening 25 may be secured to the head 16. Finally, the portion of the sheet 12 surrounding the head 16 of the stethoscope 14 may be secured to the skin of a patient in order to secure the head 16 of the stethoscope 14 to the patient's body. In this manner, the stethoscope 14 is maintained on the patient's body for use of the stethoscope for an extended period of time during a surgical procedure.

Figure 4:
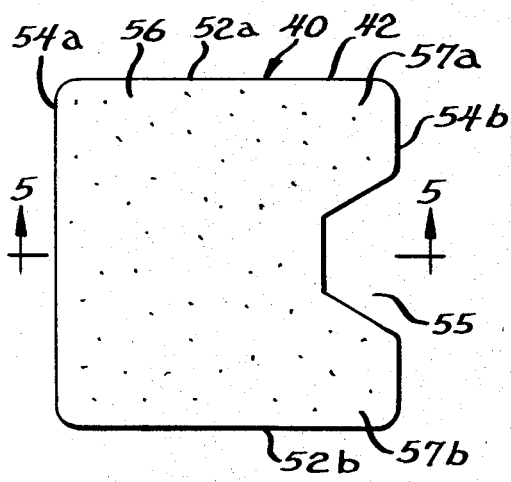
FIG. 4 is a plan view of another embodiment of a securing pad of the present invention.
Figure 5:
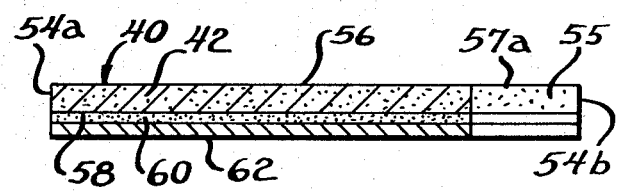
FIG. 5 is a sectional view taken substantially as indicated along the line 5—5 of FIG. 4.
Figure 6:
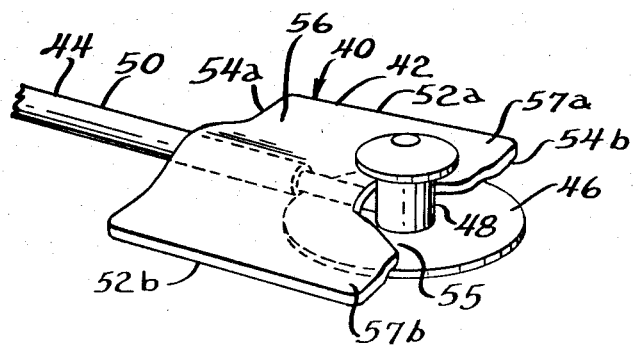
FIG. 6 is a fragmentary perspective view showing the use of the pad of FIGS. 4 and 5 to secure a stethoscope to a patient's skin.

Another embodiment of the present invention is illustrated in FIGS. 4-6. In this embodiment, there is shown a pad generally designated 40 comprising a generally rectangular sheet 42 of flexible material, such as closed cell polyethylene foam, as previously described. This embodiment of the pad 40 is utilized with a stethoscope 44 of the type having a head 46, a stem 48 connected to the head 46, and a tube 50 connected to the stem 48 at a location adjacent the head 46.

The sheet 42 has a pair of opposed side edges 52a and 52b, and a pair of opposed end edges 54a and 54b connecting the side edges 52a and b. As shown, the sheet 42 has a cut-out 55 in the end edge 54b at a location intermediate the side edges 52a and b, and defining a pair of flaps 57a and 57b intermediate the cut-out 55 and side edges 52a and b. The sheet 12 has a back surface 56, an opposed front surface 58, and a pressure-sensitive adhesive 60 on the front surface 58 of the sheet 42. The pad 40 also has a release sheet 62 of suitable material releasably covering the adhesive 60.

In use, the release sheet 62 is peeled from the adhesive 60 in order to expose the adhesive 60 on the front surface 58 of the sheet 42. Next, the head 46 of the stethoscope 44 is placed against the patient's skin. The sheet 42 is placed over the tube 50 of the stethoscope 44, with the stem 48 of the stethoscope 44 being received in the cut-out 55, after which the sheet 42 is pressed against the stethoscope 44 to secure the flaps 57a and b against the head 46 and the sheet 42 against the tube 50 of the stethoscope 44. Also, the remaining portion of the sheet 42 is secured by the adhesive 60 against the patient's skin surrounding the tube 50 and head 46 of the stethoscope 44 in order to maintain the stethoscope 44 against the patient's skin for an extended period of time during a surgical procedure.

The foregoing detailed description is given for clearness of understanding only, and no unnecessary limitations should be understood therefrom, as modifications will be obvious to those skilled in the art.

We claim:

1. A securing pad, comprising:
    a stethoscope having a head for contacting a a patient's skin; and
    a generally annular sheet of flexible material larger than the head and having a circular outer edge larger than said head, a circular inner edge defining an opening smaller than the head of the stethoscope, a slot extending from the outer edge to the inner edge, a back surface, a front surface, and adhesive on the front surface of the sheet, said stethoscope being passed through said slot to position the head in said opening.

2. The pad of claim 1 wherein said sheet comprises a foam material.

3. The pad of claim 1 wherein said slot is tapered from the outer edge to the inner edge.

4. The pad of claim 1 including a release sheet releasably covering the adhesive.

5. A securing pad comprising:
    a stethoscope having a head for contacting a patient's skin, and a tube adjacent the head; and
    a generally rectangular sheet of flexible material having a pair of side edges, a pair of end edges connecting the side edges, a cut-out in one of said end edges intermediate the side edges and defining a pair of flaps intermediate the cut-out and side edges, a back surface, a front surface, and adhesive on the front surface of the sheet, said head being received in the cut-out with said tube extending beneath the sheet from the cut-out to the other end edge of the sheet.

6. The pad of claim 5 wherein said sheet comprises a foam material.

7. The pad of claim 5 including a release sheet releasably covering said adhesive.

* * * * *